United States Patent [19]

Krämer et al.

[11] 4,419,361
[45] Dec. 6, 1983

[54] COMBATING FUNGI WITH 1-PHENOXY-1-IMIDAZOL-1-yl-4-FLUORO-BUTANE DERIVATIVES

[75] Inventors: Wolfgang Krämer, Wuppertal; Karl H. Büchel, Wuppertal; Jörg Stetter, Wuppertal; Paul-Ernst Frohberger, Leverkusen; Wilhelm Brandes, Leichlingen; Hans Scheinpflug, Leverkusen, all of Fed. Rep. of Germany

[73] Assignee: Bayer Aktiengesellschaft, Leverkusen, Fed. Rep. of Germany

[21] Appl. No.: 321,642

[22] Filed: Nov. 16, 1981

Related U.S. Application Data

[63] Continuation of Ser. No. 142,536, Apr. 21, 1980, abandoned.

[30] Foreign Application Priority Data

May 10, 1979 [DE] Fed. Rep. of Germany ....... 2918893

[51] Int. Cl.³ ..................... A01N 43/50; C07D 233/60
[52] U.S. Cl. ................. 424/273 R; 548/341; 548/101; 548/109; 424/245
[58] Field of Search ....... 548/341, 101, 109; 424/245, 273 R

[56] References Cited

U.S. PATENT DOCUMENTS 4,005,083  1/1977  Büchel et al. ............... 548/101
4,255,434  3/1981  Kramer et al. ............... 424/269

FOREIGN PATENT DOCUMENTS 2632602  1/1978  Fed. Rep. of Germany .

*Primary Examiner*—Henry R. Jiles
*Assistant Examiner*—Natalia Harkaway
*Attorney, Agent, or Firm*—Sprung, Horn, Kramer & Woods

[57] ABSTRACT

1-Phenoxy-1-imidazol-1-yl-4-fluoro-butane derivatives of the formula

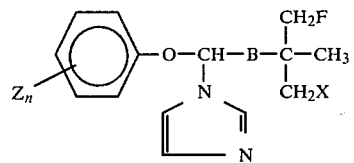

in which
  B is —CO— or —CH(OH)—,
  X is hydrogen or fluorine,
  Z each independently is halogen, alkyl, nitro, cyano, alkoxy-carbonyl or optionally substituted phenyl, and
  n is 0, 1, 2 or 3, or an acid or metal salt adduct thereof, which possess fungicidal properties.

6 Claims, No Drawings

COMBATING FUNGI WITH 1-PHENOXY -1-IMIDAZOL-1-yl-4-FLUORO-BUTANE DERIVATIVES

This is a continuation division of application Ser. No. 142,536, filed Apr. 21, 1980 now abandoned.

The present invention relates to certain new fluorinated 1-imidazolyl-butane derivatives, to a process for their preparation and to their use as fungicides.

It has already been disclosed that certain chlorinated and brominated 1-imidazolyl-butane derivatives have good fungicidal properties (see DE-OS (German Published Specification) 2,632,602. However, the action of these compounds is not always completely satisfactory, especially when small amounts and low concentrations are applied.

The present invention now provides, as new compounds, the fluorinated 1-imidazolyl-butane derivatives of the general formula

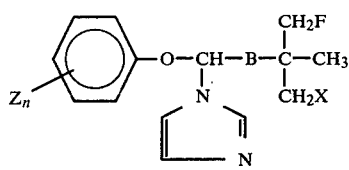

in which
B represents the keto group or the CH(OH)— grouping,
X represents hydrogen or fluorine,
Z represents halogen, alkyl, nitro, cyano, alkxoycarbonyl or optionally substituted phenyl and
n represents 0, 1, 2 or 3, the substituent Z being selected independently when n is 2 or 3,
and acid and metal salt adducts thereof.

Those compounds of the formula (I) in which R represents the CH(OH)—grouping have two asymmetric carbon atoms; they can therefore exist in the form of the two geometric isomers (threo form and erythro form), which can be obtained in varying proportions. In both cases, they exist in the form of optical isomers. All the isomers are comprehended by the formula (I).

The invention also provides a process for the preparation of a fluorinated 1-imidazolyl-butane derivative of the formula (I), in which a halogeno-ether ketone of the general formula

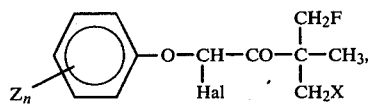

in which
X, Z and n have the meanings indicated above and
Hal represents halogen, preferably chlorine or bromine,
is reacted with imidazole in the presence of an acid-binding agent and if appropriate in the presence of a diluent, and, if required, the resulting keto derivative is reduced; the reduction can be accomplished by known methods in the customary manner.

An acid or a metal salt can optionally be added onto the compound of the formula (I) thus obtained.

The new fluorinated 1-imidazolyl-butane derivatives have powerful fungicidal properties. Surprisingly, the compounds according to the invention exhibit a considerably more powerful action than the chlorinated and brominated 1-imidazolyl-butane derivatives known from the state of the art, which are very closely related compounds chemically and from the point of view of their action. The substances according to the invention thus represent an enrichment of the art.

The formula (I) provides a general definition of the fluorinated 1-imidazolyl-butane derivatives according to the invention. In this formula, Z preferably represents halogen, alkyl with 1 to 4 carbon atoms, nitro, cyano, alkoxycarbonyl with 1 to 4 carbon atoms in the alkyl part or phenyl which is optionally substituted by halogen.

Those fluorinated 1-imidazolyl-butane derivatives (I) in which Z represents fluorine, chlorine, bromine, iodine, methyl, ethyl, nitro, cyano, methoxycarbonyl, ethoxycarbonyl, phenyl or chlorophenyl and n represents 0, 1 or 2 are very particularly preferred.

The following compounds of the general formula (I) may be mentioned specifically, in addition to the compounds mentioned later in the preparative examples:

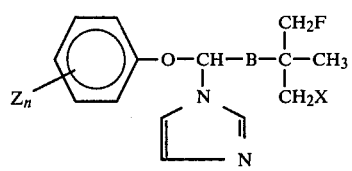

| $Z_n$ | X | B |
|---|---|---|
| — | H | CO |
| 2-F | H | CO |
| 3-F | H | CO |
| 4-F | H | CO |
| 2-Cl | H | CO |
| 3-Cl | H | CO |
| 2-Br | H | CO |
| 3-Br | H | CO |
| 2-CH$_3$ | H | CO |
| 4-CH$_3$ | H | CO |
| 2-—⟨O⟩ | H | CO |
| 4-—⟨O⟩ | H | CO |
| 4-—⟨O⟩—Cl | H | CO |
| 2-NO$_2$ | H | CO |
| 4-CN | H | CO |
| 4-COOCH$_3$ | H | CO |
| 4-COOC$_2$H$_5$ | H | CO |
| 4-I | H | CO |
| 4-Cl, 2-CH$_3$ | H | CO |
| 4-CH$_3$, 2-Cl | H | CO |
| — | H | CH(OH) |
| 2-F | H | CH(OH) |
| 3-F | H | CH(OH) |
| 4-F | H | CH(OH) |
| 2-Cl | H | CH(OH) |
| 3-Cl | H | CH(OH) |
| 2-Br | H | CH(OH) |
| 3-Br | H | CH(OH) |
| 2-CH$_3$ | H | CH(OH) |
| 4-CH$_3$ | H | CH(OH) |
| 2- | H | CH(OH) |

-continued

| $Z_n$ | X | B |
|---|---|---|
| 4-⟨phenyl⟩ | H | CH(OH) |
| 4-⟨phenyl⟩-Cl | H | CH(OH) |
| 2-NO$_2$ | H | CH(OH) |
| 4-CN | H | CH(OH) |
| 4-COOCH$_3$ | H | CH(OH) |
| 4-COOC$_2$H$_5$ | H | CH(OH) |
| 4-I | H | CH(OH) |
| 4-Cl, 2-CH$_3$ | H | CH(OH) |
| 4-CH$_3$, 2-Cl | H | CH(OH) |
| — | F | CO |
| 2-F | F | CO |
| 3-F | F | CO |
| 3-Cl | F | CO |
| 2-Br | F | CO |
| 3-Br | F | CO |
| 4-Br | F | CO |
| 2-CH$_3$ | F | CO |
| 4-CH$_3$ | F | CO |
| 2-⟨phenyl⟩ | F | CO |
| 4-⟨phenyl⟩-Cl | F | CO |
| 2-NO$_2$ | F | CO |
| 4-NO$_2$ | F | CO |
| 4-CN | F | CO |
| 4-COOCH$_3$ | F | CO |
| 4-COOC$_2$H$_5$ | F | CO |
| 4-I | F | CO |
| 4-Cl, 2-CH$_3$ | F | CO |
| — | F | CH(OH) |
| 2-F | F | CH(OH) |
| 3-F | F | CH(OH) |
| 3-Cl | F | CH(OH) |
| 2-Br | F | CH(OH) |
| 3-Br | F | CH(OH) |
| 4-Br | F | CH(OH) |
| 2-CH$_3$ | F | CH(OH) |
| 4-CH$_3$ | F | CH(OH) |
| 2-⟨phenyl⟩ | F | CH(OH) |
| 4-⟨phenyl⟩-Cl | F | CH(OH) |
| 2-NO$_2$ | F | CH(OH) |
| 4-NO$_2$ | F | CH(OH) |
| 4-CN | F | CH(OH) |
| 4-COOCH$_3$ | F | CH(OH) |
| 4-COOC$_2$H$_5$ | F | CH(OH) |
| 4-I | F | CH(OH) |
| 4-Cl, 2-CH$_3$ | F | CH(OH) |
| 4-CH$_3$, 2-Cl | F | CH(OH) |
| 4-F | F | CH(OH) |

If, for example, 1-bromo-1-(4-chlorophenoxy)-3,3-dimethyl-4-fluoro-butan-2-one and imidazole are used as starting substances, the course of the synthesis can be represented by the following equation:

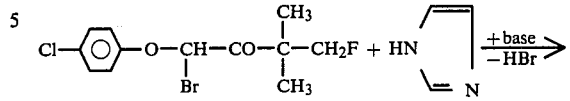

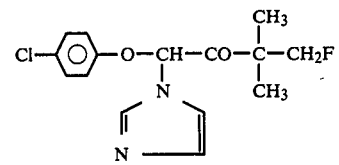

If 1-(4-chlorophenoxy)-3,3-dimethyl-4-fluoro-1-(imidazol-1-yl)-butan-2-one and sodium borohydride are used as starting substances, the course of the reduction reaction can be represented by the following equation:

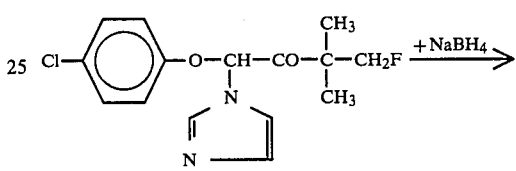

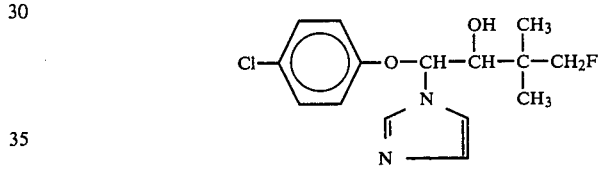

The formula (II) provides a general definition of the halogeno-ether ketones to be used as starting substances in carrying out the process according to the invention. In this formula, Z and the index n preferably have those meanings which have already been mentioned as preferred in connection with the description of the substances of the formula (I).

The halogeno-ether ketones of the formula (II) have not hitherto been disclosed in the literature. However, they can be obtained by known processes (see, for example, DE-OS (German Published Specification) 2,632,603, for example by reacting known phenols of the general formula

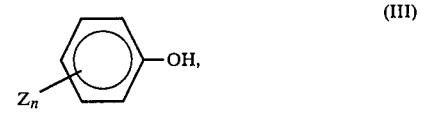

in which
Z and n have the meanings indicated above, with a halogenoketone of the formula

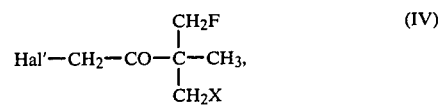

in which
X has the meaning indicated above and

Hal' represents chlorine or bromine.

The active hydrogen atom which still remains is then replaced by halogen in the customary manner (see also the preparative examples).

Likewise, the halogenoketones of the formula (IV) have not been described in the literature hitherto. However, they can be obtained in a generally customary and known manner, by adding chlorine or bromine to fluorine derivatives of 3,3-dimethyl-butan-2-one, of the general formula

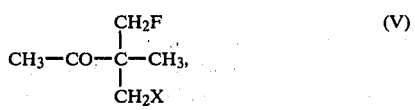
(V)

in which

X has the meaning indicated above, in the presence of an inert organic solvent, for example an ether or chlorinated hydrocarbon, at room temperature (see also the preparative examples), or by reacting the above fluorine derivatives with customary chlorinating agents, for example sulphuryl chloride, at 20° to 60° C.

The fluorine derivatives of 3,3-dimethyl-butan-2-one, of the formula (V), have likewise not been described in the literature hitherto. However, they are the subject of German Patent Application P2843767 of 6.10.1978. The fluorine derivatives of 3,3-dimethyl-butan-2-one, of the formula (V), are obtained when sulphonic acid esters of the general formula

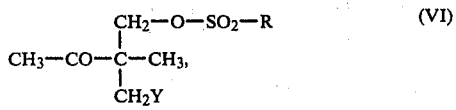
(VI)

in which

R represents alkyl with 1 to 4 carbon atoms, especially methyl, or aryl with 6 to 12 carbon atoms, especially phenyl or tolyl, and Y represents hydrogen or the group —O—SO$_2$—R, are reacted with metal fluorides, for example sodium fluoride and potassium fluoride, in the presence of a polar organic solvent, for example di-, tri- or tetra-ethylene glycol, at a temperature between 80° and 250° C. (see also the preparative examples).

Sulphonic acid esters of the formula (VI) are known (J.Org.Chem. 35, 2391 (1970)) and can be prepared by processes known from the literature, from the corresponding hydroxybutanones and sulphochlorides in the presence of bases (see, for example, Houben-Weyl, Methoden der Org. Chemie (Methods of Organic Chemistry), Volume IX, pages 388 and 663, and the statements in the preparative examples).

Possible diluents for the reaction according to the invention are inert organic solvents. These include, as preferences, ketones, such as diethyl ketone, and in particular acetone and methyl ethyl ketone; nitriles, such as propionitrile, and in particular acetonitrile; alcohols, such as ethanol or isopropanol; ethers, such as tetrahydrofuran or dioxane; benzene; toluene; formamides, such as, in particular, dimethylformamide; and halogenated hydrocarbons.

The reaction according to the invention is carried out in the presence of an acid-binding agent. It is possible to add any of the inorganic or organic acid-binding agents which can customarily be used, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine and N,N-dimethylbenzylamine, and furthermore pyridine and diazabicyclooctane.

An appropriate excess of imidazole is preferably used.

The reaction temperatures can be varied within a substantial range. In general, the reaction is carried out at from 20° to 150° C., preferably at from 60° to 120° C. If a solvent is present, the reaction is appropriately carried out at the boiling point of the particular solvent.

In carrying out the process according to the invention, 2 mols of imidazole and 1 to 2 mols of acid-binding agent are preferably employed per mol of the compound of the formula (II). To isolate the resultant compound of the formula (I), the solvent is distilled off, the residue is taken up in an organic solvent and the mixture is washed with water. The organic phase is dried over sodium sulphate and freed from solvent in vacuo. The residue is purified by distillation or recrystallization or salt formation and recrystallization.

The reduction according to the invention can be carried out in the customary manner, for example by reaction with a complex hydride, if appropriate in the presence of a diluent, or by reaction with aluminum isopropylate in the presence of a diluent.

If a complex hydride is used, possible diluents for the reaction according to the invention are polar organic solvents. These include, as preferences, alcohols, such as methanol, ethanol, butanol or isopropanol, and ethers, such as diethyl ether or tetrahydrofuran. The reaction is in general carried out at from 0° to 30° C., preferably at 0° to 20° C. For the reaction, about 1 mol of a complex hydride, such as sodium borohydride or lithium alanate, is employed per mol of the ketone of the formula (I). To isolate the reduced compound of the formula (I), the residue is taken up in dilute hydrochloric acid and the mixture is then rendered alkaline and extracted with an organic solvent. Further working up is effected in the customary manner.

If aluminum isopropylate is used, preferred diluents for the reaction according to the invention are alcohols, such as isopropanol, or inert hydrocarbons, such as benzene. The reaction temperatures can again be varied within a substantial range; in general, the reaction is carried out at from 20° to 120° C., preferably at 50° to 100° C. For carrying out the reaction, 0.3 to 2 mols of aluminum isopropylate are preferably employed per mol of the ketone of the formula (I). To isolate the reduced compound of the formula (I), the excess solvent is removed in vacuo and the aluminum compounds formed are decomposed with dilute sulphuric acid or sodium hydroxide solution. Further working up is effected in the customary manner.

Any of the physiologically acceptable acids can be used for the preparation of acid addition salts of the compounds of the formula (I). These acids include, as preferences, hydrogen halide acids (for example hydrobromic acid and in particular hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent or by recrystallization.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are derived from physiologically acceptable acids. These include, as preferences, hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating powdery mildew of cucumber (*Erysiphe cichoracearum*), and against cereal diseases, such as against powdery mildew of cereal, cereal rust and powdery mildew of barley.

It should be emphasized that the active compounds according to the invention not only display a protective action but also have a systemic action. Thus, it is possible to protect plants from fungal attack when the active compound is fed to the above-ground parts of the plant via the soil and the root or via the seed.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

(a)

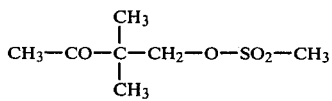

232 g (2 mol) of 3,3-dimethyl-4-hydroxy-2-butanone (for the preparation, see Beilstein H 1 E III 3239, IV 4030 and Bull.Soc. Chim. France 1964, 2849) were reacted with 229 g (2 mol) of methanesulphonyl chloride in 700 ml of absolute pyridine at 0° to 5° C. After leaving the mixture to stand at 20° C. for 12 hours, it was diluted with methylene chloride and extracted by shaking with ice-water. The organic phase was dried, and freed from solvent in vacuo, and the residue was fractionated over a column. 332 g (86% of theory) of 2,2-dimethyl-3-oxo-butyl methanesulphonate of boiling point 106°–120° C./0.12 mm Hg were obtained.

(b)

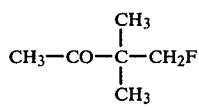

38.8 g (0.2 mol) of 2,2-dimethyl-2-oxobutyl methanesulphonate were added dropwise to a suspension, in a three-necked stirred flask with a descending condenser, of 23.2 g (0.4 mol) of dry potassium fluoride in 400 ml of distilled tetraethylene glycol at 160° C. and under 20 mbar in the course of 2 hours and the mixture was subequently stirred for a further 2 hours. The reaction product which had distilled out was condensed and collected in a descending condenser and subsequent cold trap. 20.9 g (89% of theory) of 3,3-dimethyl-4-fluoro-2-butanone of boiling point 130°–134° C. were obtained.

(c)

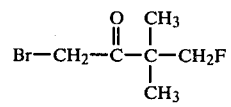

118 g (1 mol) of 3,3-dimethyl-4-fluoro-2-butanone were dissolved in 600 ml of chloroform, and 52 ml of bromine were added dropwise at a rate such that decolorization continuously occurred. When the addition had ended, the mixture was further stirred for 30 minutes. Thereafter, it was concentrated by distilling off the solvent in vacuo. 197 g (100% of theory) of 1-bromo-3,3-dimethyl-4-fluoro-2-butanone of boiling point 85°–90° C./12 mm Hg column, which could be further reacted in crude form, were obtained.

(d)

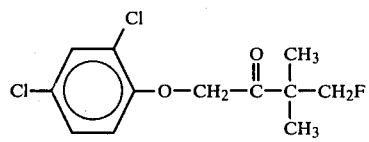

A solution of 197 g (1 mol) of 1-bromo-3,3-dimethyl-4-fluoro-2-butanone in 100 ml of acetone was added dropwise, at the boiling point, to 140 g (1 mol) of potassium carbonate and 163 g (1 mol) of 2,4-dichlorophenol in 1,000 ml of acetone. The mixture was stirred under reflux for 20 hours, cooled and filtered. The filtrate was concentrated by distilling off the acetone under a water-pump vacuum. The residue was dissolved in 500 ml of toluene, washed with 500 ml of 10% strength sodium hydroxide solution and with two 250 ml portions of water, dried over sodium sulphate and concentrated by distilling off the toluene under a waterpump vacuum. 244.6 g (88% of theory) of 1-(2,4-dichlorophenoxy)-3,3-dimethyl-4-fluoro-2-butanone were obtained as a highly viscous oil which could be further reacted in crude form.

(e)

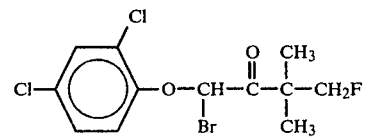

244.6 g (0.88 mol) of crude 1-(2,4-dichloro-phenoxy)-3,3-dimethyl-4-fluoro-2-butanone were dissolved in 700 ml of chloroform, and 46 ml of bromine were added dropwise at 30° C. at a rate such that decolorization continuously occurred. When the addition had ended, the mixture was subsequently stirred for 30 minutes and then concentrated by distilling off the chloroform in vacuo. 315 g (100% of theory) of 1-bromo-1-(2,4-dichlorophenoxy)-3,3-dimethyl-4-fluoro-2-butanone were obtained as a viscous oil which could be further reacted in crude form.

(f)

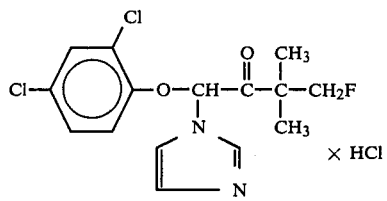 (1)
× HCl 157.5 g (0.44 mol) of 1-bromo-1-(2,4-dichlorophenoxy)-3,3-dimethyl-4-fluoro-2-butanone were dissolved in 500 ml of acetonitrile and the solution was added dropwise to a solution of 109 g (1.6 mol) of imidazole in 600 ml of acetonitrile. The mixture was heated under reflux for 10 hours. Thereafter, the solvent was distilled off under a waterpump vacuum, the residue was taken up in 1,000 ml of methylene chloride and the methylene chloride mixture was washed three times with 500 ml of water each time. The organic phase was dried over sodium sulphate, filtered and concentrated under a waterpump vacuum by distilling off the solvent. The residue was dissolved in 500 ml of ethanol, 40 ml each of concentrated hydrochloric acid were added and the solvent was distilled off under a waterpump vacuum. The residue was stirred with 500 ml of ether, whereupon it crystallized. 66 g (39.3% of theory) of 1-(2,4-dichloro-phenoxy)-3,3-dimethyl-4-fluoro-1-(imidazol-1-yl)-2-butanone hydrochloride of melting point 91°–110° C. were obtained.

Example 2

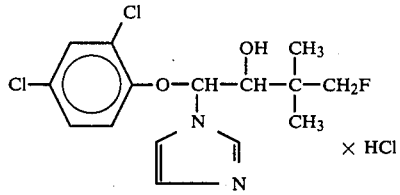 (2)
× HCl 44 g (0.1275 mol) of 1-(2,4-dichlorophenoxy)-3,3-dimethyl-4-fluoro-1-(imidazol-1-yl)-2-butanone (Example 1) were dissolved in 300 ml of methanol, and 6.3 g of sodium borohydride were added at 0° to 5° C. The mixture was subsequently stirred at room temperature for 15 hours, 60 ml of concentrated hydrochloric acid were added dropwise, whilst cooling with ice, the mixture was stirred at room temperature for 10 hours and the solvent was distilled off under a waterpump vacuum. The residue was taken up in 250 ml of methylene chloride, the methylene chloride mixture was stirred into 500 ml of aqueous, saturated sodium bicarbonate solution, the methylene chloride phase was separated off and washed three times with 100 ml of water each time, the organic phase was dried over sodium sulphate and the solvent was distilled off. The oil which remained was taken up in 200 ml of ether, 50 ml of ethereal hydrochloric acid were added and the solvent was distilled off. 28.2 g (58% of theory) of 1-(2,4-dichlorophenoxy)-3,3-dimethyl-4-fluoro-1-(imidazol-1-yl)-2-butanol hydrochloride of melting point 184°–210° C. were obtained as a diastereomer mixture.

Example 3

(a)

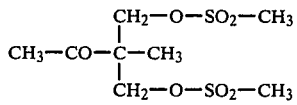

66 g (0.5 mol) of 3-oxa-2,2-bis-(hydroxymethyl)butane (for the preparation, see Beilstein H 1, E III 3306, IV 4132 and J.Chem.Soc., London, 1932, 2671) were dissolved in 300 ml of 1,2-dichloroethane, 114.5 g (1 mol) of methanesulphonic acid chloride were added dropwise, and 158 g (2 mol) of pyridine were added dropwise at 0° to 5° C. The batch was subsequently stirred at room temperature for 15 hours and then discharged onto 600 ml of ice-water and 100 ml of concentrated hydrochloric acid. A solid thereby precipitated and was filtered off. The aqueous phase was extracted with 1,000 ml of methylene chloride; the solid was dissolved in the methylene chloride phase, the organic phase was dried over sodium sulphate, the solvent was distilled off under a waterpump vacuum and the residue was suspended in 200 ml of ether. The residue was filtered off and washed with 100 ml of ether.

100 g (about 70% of theory) of 2-acetyl-2-methylpropane-1,3-diol bis-methanesulphonate of melting point 105° to 108° C. were obtained.

(b)

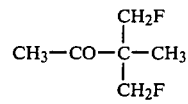

400 ml of tetraethylene glycol and 46.4 g (0.8 mol) of potassium fluoride were initially introduced into a three-necked flask with a stirrer, dropping funnel and Liebig condenser with a cooled receiver and the mixture was heated to 170° C. A waterpump vacuum (pressure: about 20 to 30 mbar) was applied at the adaptor of the Liebig condenser. 57.6 g (0.2 mol) of 2-acetyl-2-methyl-propane-1,3-diol bis-methanesulphonate, dissolved in 100 ml of tetraethylene glycol, were then added dropwise in the course of 45 minutes. The 3,3-bis-fluoromethyl-butan-2-one formed was distilled off into the cooled receiver during the reaction. After the dropwise addition, distillation was continued at 175° C. for a further hour.

The distillate collected was then redistilled. 14 g (about 51.5% of theory) of 3,3-bis-fluoromethyl-butan-2-one of boiling point 43°–46° C./12 mm Hg were obtained.

(c)

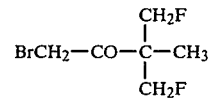

This compound was prepared according to Example 1c by reacting 3,3-bis-fluoromethyl-butan-2-one with bromine.

(d)

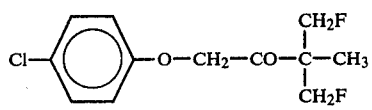

This compound was prepared according to Example 1d by reacting p-chlorophenol with 3,3-bisfluoromethyl-1-bromo-butan-2-one.

(e)

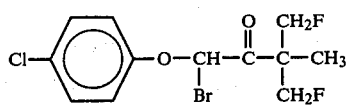

This compound was prepared according to Example 1e by reacting 3,3-bis-fluoromethyl-1-(4-chlorophenoxy)-butan-2-one with bromine.

(f)

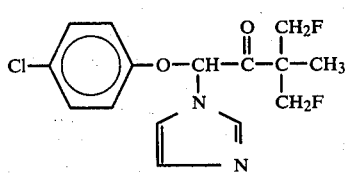
(3)

61.5 g (0.18 mol) of 3,3-bis-fluoromethyl-1-bromo-1-(4-chlorophenoxy)-butan-2-one were stirred with 27.2 g (0.4 mol) of imidazole in 500 ml of acetonitrile at 45° C. for 4 hours. The solvent was distilled off under a water-pump vacuum, the oil which remained was taken up in 500 ml of methylene chloride, the organic phase was washed twice with 1,000 ml of water and dried over sodium sulphate and the solvent was distilled off. The oil was taken up in acetone, 36 g (0.1 mol) of 1,5-naphthalenedisulphonic acid tetrahydrate were added and the precipitate formed was filtered off. The precipitate (the 1,5-naphthalenedisulphonate of the compound of Example 3) was treated with sodium bicarbonate solution. 14 g (24% of theory) of 3,3-bis-fluoromethyl-1-(4-chlorophenoxy)-1-(imidazol-1-yl)-butan-2-one were obtained as a viscous oil.

The following compound of the general formula

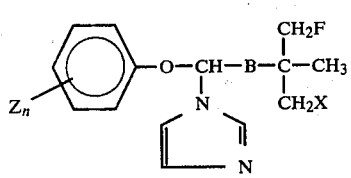
(I)

were each obtained in a manner corresponding to that described above:

| Compound No. | $Z_n$ | B | X | Melting point (°C.) or boiling point (°C./mm Hg) |
|---|---|---|---|---|
| 4 | 4-Cl | CO | H | Oil |
| 5 | 4-Cl | CO | H | 260-65 (× ½ NDS) |
| 6 | 4-Br | CO | H | 142 (× HCl) |
| 7 | 4-C₆H₅ | CO | F | Oil |
| 8 | 4-Cl | CO | F | 250 (× ½ NDS) |
| 9 | 4-F | CO | F | 245-50 (× ½ NDS) |
| 10 | 4-Cl | CH(OH) | H | 148-52 |
| 11 | 4-Br | CH(OH) | H | 160-62 |
| 12 | 4-C₆H₅ | CH(OH) | F | 151 |
| 13 | 4-Cl | CH(OH) | F | 137 |
| 14 | 2-Cl | CO | F | 206-10 (× ½ NDS) |
| 15 | 2,3-Cl₂ | CO | F | 198-202 (× ½ NDS) |
| 16 | 2-Cl, 4-CH₃ | CO | F | 204 (× ½ NDS) |
| 17 | 2,4-Cl₂ | CH(OH) | F | 106-09 (A-Form) |
| 18 | 2-Cl | CH(OH) | F | 110-19 (A-Form) |
| 19 | 4-C₆H₅ | CO | H | 87-106 |
| 20 | 4-C₆H₅ | CH(OH) | H | 120-22 |
| 21 | 4-F | CH(OH) | F | 96-112 |
| 22 | 2,4-Cl₂ | CO | F | 124 |
| 23 | 4-Br | CO | F | 260 (× ½ NDS) |
| 24 | 4-(C₆H₄-Cl) | CO | F | oil |
| 25 | 3-Cl | CO | F | oil |
| 26 | 4-Br | CH(OH) | F | 161-63 |
| 27 | 4-Cl, 2-CH₃ | CH(OH) | F | 108-15 |
| 28 | 4-COOC₂H₅ | CO | F | 243-45 (× ½ NDS) |
| 29 | 4-(C₆H₄-Cl) | CH(OH) | F | 151-65 |
| 30 | 3-Cl | CH(OH) | F | 239-43 (× ½ NDS) |
| 31 | 4-CH₃ | CH(OH) | F | 143-47 |
| 32 | 4-NO₂ | CH(OH) | F | 168-73 |
| 33 | 4-CH₃ | CO | F | 260 (× ½ NDS) |
| 34 | 4-NO₂ | CO | F | >260 (× ½ NDS) |
| 35 | 4-COOCH₃ | CO | F | 250-52 (× ½ NDS) |
| 36 | 2-F | CO | H | 135 (× HCl) |
| 37 | — | CO | H | 153 (× HCl) |
| 38 | — | CH(OH) | H | 137 |
| 39 | 2-C₆H₅ | CO | F | 223-25 (× ½ NDS) |
| 40 | 4-CN | CO | F | 256 (× ½ NDS) |
| 41 | 2-C₆H₅ | CH(OH) | F | 97-107 |
| 42 | 4-COOCH₃ | CH(OH) | F | 135-47 |
| 43 | 3-Br | CO | F | 245 (× ½ NDS) |
| 44 | 4-COOC₂H₅ | CH(OH) | F | 123-27 |
| 45 | 4-CN | CH(OH) | F | 107-17 |
| 46 | 3,4-Cl₂ | CO | H | 156-60 (dec.) (× HCl) |
| 47 | 2-NO₂ | CH(OH) | F | 203-10 (× ½ NDS) |
| 48 | 2-Br | CH(OH) | F | 116-20 |
| 49 | 4-I | CH(OH) | F | 176-80 |
| 50 | 3-Br | CH(OH) | F | 117-22 |
| 51 | 2-NO₂ | CO | F | 230 (× ½ NDS) |
| 52 | 2-Br | CO | F | 212-15 (× ½ NDS) |

-continued

| Compound No. | $Z_n$ | B | X | Melting point (°C.) or boiling point (°C./mm Hg) |
|---|---|---|---|---|
| 53 | 4-I | CO | F | 255 (× ½ NDS) |
| 54 | 3,4-Cl$_2$ | CH(OH) | H | 203 |

NDS = 1,5-naphthalenedisulphonic acid
A form = one of the two possible geometric isomers.

The fungicidal activity of the compounds of this invention is illustrated by the following examples wherein compounds according to the present invention are each identified by the number (given in brackets) from the preparative examples hereinabove.

The known comparison compounds are identified as follows:

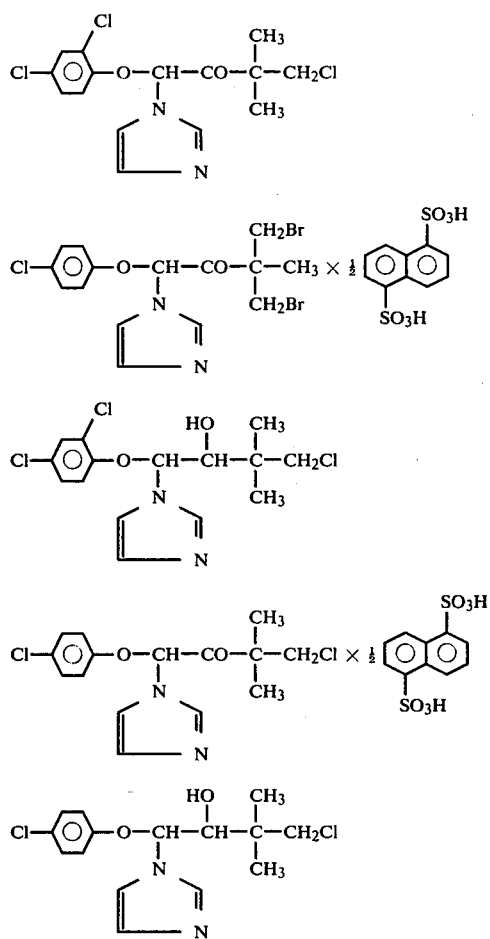

Example 4

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of Erysiphe graminis var. hordei.

After 6 days' dwell time of the plants at a temperature of 21–22 deg.C. and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compounds showed a very good action which was superior to that of the compounds (A) and (B) known from the prior art: compounds (1), (8), (4), (9), (6) and (2).

Example 5

Powdery mildew of barley (Erysiphe graminis var. hordei)

(fungal disease of cereal shoots)/systemic

The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in the flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of Erysiphe graminis var. hordei and grown on at 21–22 deg.C. and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

In this test, for example, the following compounds showed a very good action which was superior to that of the compounds (A), (B) and (C) known from the prior art: (1), (2), (8), (4), (5) and (6).

Example 6

Shoot treatment test/cereal rust (leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of Puccinia recondita in 0.1% strength aqueous agar. After the spore suspension had dried on, the wheat plants were sprayed with the preparation of active compound until dew-moist and were placed, for incubation, in a greenhouse for 24 hours at about 20 deg.C. and 100% relative atmospheric humidity.

After 10 days' dwell time of the plants at a temperature of 20 deg.C. and 80-90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

In this test, for example, the following compounds showed a very good action which was superior to that of the compounds (D) and (E) from the prior art: compounds (5) and (10)

Example 7

Erysiphe test (cucumber)/protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cumumber plants remained in a greenhouse for 24 hours to dry. They were then, for the purpose of inoculation, dusted with conidia of the fungus *Erysiphe cichoracearum*. The plants were subsequently placed in a greenhouse at 23-24 degrees C. and at a relative atmospheric humidity of about 75%.

After 12 days, the infection of the cucumber plants was determined. The assessment data were converted to percent infection. 0% meant no infection; 100% meant that the plants were totally infected.

In this test, for example, the following compounds showed a very good action which was superior to that of the compound (D) known from the prior art: compounds (10), (1), (8) and (4).

It will be appreciated that the instant specification and examples are set forth by way of illustration and not limitation, and that various modifications and changes may be made without departing from the spirit and scope of the present invention.

What is claimed is:

1. A 1-phenoxy-1-imidazol-1-yl-4-fluoro-butane derivative selected from the group consisting of

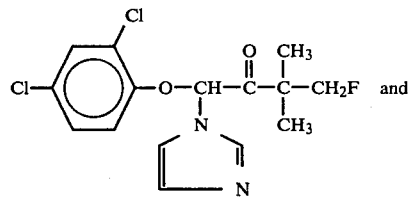

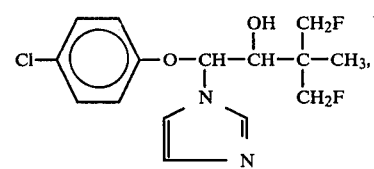

or an acid adduct thereof.

2. A compound or adduct thereof according to claim 1, wherein such compound is 1-(2,4-dichloro-phenoxy)-3,3-dimethyl-4-fluoro-1-(imidazol-1-yl)-2-butanone of the formula

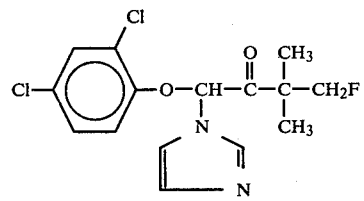

3. A compound or adduct thereof according to claim 1, wherein such compund is 3,3-bis-fluoromethyl-1-(4-chlorophenoxy)-1-(imidazol-1-yl)-butan-2-ol of the formula

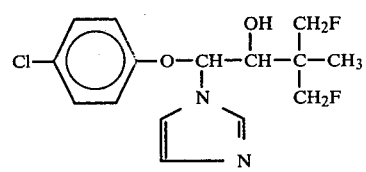

4. A fungicidal composition containing as active ingredient a fungicidally effective amount of a compound or adduct according to claim 1 in admixture with a diluent.

5. A method of combating fungi which comprises applying to the fungi, or to a habitat thereof, a fungicidally effective amount of a compound or adduct according to claim 1.

6. The method according to claim 5, in which said compound is
   1-(2,4-dichloro-phenoxy)-3,3-dimethyl-4-fluoro-1-(imidazol-1-yl)-2-butanone, or
   3,3-bis-fluoromethyl-1-(4-chlorophenoxy)-1-(imidazol-1-yl)-butan-2-ol.

* * * * *